United States Patent
Harding

(10) Patent No.: US 10,215,879 B2
(45) Date of Patent: Feb. 26, 2019

(54) SYSTEM FOR DETECTING COUNTERFEIT GOODS AND METHOD OF OPERATING THE SAME

(71) Applicant: MORPHO DETECTION, LLC, Newark, CA (US)

(72) Inventor: Geoffrey Harding, Hamburg (DE)

(73) Assignee: MORPHO DETECTION, LLC, Newark, CA (US)

( * ) Notice: Subject to any disclaimer, the term of this patent is extended or adjusted under 35 U.S.C. 154(b) by 722 days.

(21) Appl. No.: 14/706,538

(22) Filed: May 7, 2015

(65) Prior Publication Data
US 2016/0327660 A1 Nov. 10, 2016

(51) Int. Cl.
*G01V 5/12* (2006.01)
*G01V 5/00* (2006.01)

(52) U.S. Cl.
CPC .......... *G01V 5/0016* (2013.01); *G01V 5/0025* (2013.01); *G01V 5/0083* (2013.01); *G01N 2223/302* (2013.01); *G01N 2223/306* (2013.01); *G01N 2223/639* (2013.01); *G01N 2223/643* (2013.01)

(58) Field of Classification Search
CPC ....... G01N 2223/639; G01N 2223/419; G01N 23/046; G01N 23/10; G01N 2001/024; G01N 2223/643; G01N 9/24; G01N 23/087; G01N 23/02; G06T 2207/30112
See application file for complete search history.

(56) References Cited

U.S. PATENT DOCUMENTS

| 6,370,222 B1* | 4/2002 | Cornick, Jr. ......... | G01V 5/0016 378/57 |
| 6,707,879 B2* | 3/2004 | McClelland ............ | B64F 1/368 378/57 |

(Continued)

OTHER PUBLICATIONS

"XDi™ The Ultimate Automatic Type D Liquid Explosives Detection System for Checkpoints," product information brochure retrieved on Apr. 15 2015 from website http://www.morpho.com/IMG/pdf/Morpho_Detection_XDi_DAT.pdf (4 pgs).

(Continued)

*Primary Examiner* — Brooke Purinton
(74) *Attorney, Agent, or Firm* — Armstrong Teasdale LLP

(57) ABSTRACT

A computer-implemented method of handling a container includes performing a first scan of the container. The container includes objects therein. The scan includes irradiating the container with polychromatic x-rays with a first x-ray scanning system at a first geographic location and generating a first scan record using a processing device. The method also includes moving the container from the first geographic location to a second geographic location. The method further includes performing a second scan of the container including irradiating the container with polychromatic x-rays with a second x-ray scanning system at the second geographic location and generating a second scan record using a processing device. The method also includes comparing the first scan record and the second scan record. The method further includes determining the second scan record is substantially indistinguishable or distinguishable from the first scan record.

22 Claims, 8 Drawing Sheets

(56) References Cited

U.S. PATENT DOCUMENTS

| | | |
|---|---|---|
| 8,477,904 B2 | 7/2013 | Blaj |
| 9,632,206 B2 * | 4/2017 | Parikh .................. G06T 7/0004 |
| 2004/0109532 A1 * | 6/2004 | Ford ................... G01N 23/046 |
| | | 378/57 |
| 2005/0031075 A1 * | 2/2005 | Hopkins ................ A61B 6/482 |
| | | 378/57 |
| 2006/0078161 A1 * | 4/2006 | Schmiegel ........... G06K 9/3216 |
| | | 382/103 |
| 2010/0226478 A1 * | 9/2010 | Harding ................ G21K 1/025 |
| | | 378/70 |
| 2011/0188632 A1 * | 8/2011 | Harding .............. G01V 5/0016 |
| | | 378/86 |
| 2013/0156156 A1 * | 6/2013 | Roe ..................... G01V 5/0033 |
| | | 378/57 |
| 2014/0065663 A1 * | 3/2014 | Vasquez ................ G01N 21/17 |
| | | 435/29 |
| 2014/0119511 A1 | 5/2014 | Ward et al. |
| 2015/0325013 A1 * | 11/2015 | Patnaik ..................... G06T 7/11 |
| | | 345/424 |

OTHER PUBLICATIONS

Nuhu, Abdulmumin A. "Recent analytical approaches to counterfeit drug detection." Journal of Applied Pharmaceutical Science, vol. 1, No. 05 (2011), (8 pgs).

Krastev, E. et al., "Modern 2D/3D X-Ray Inspection—Emphasis on BGA, QFN, 3D Packages, and Counterfeit Components." In SMTA Pan Pacific Symposium. 2010. published Sep. 16, 2010, (7 pgs).

* cited by examiner

SYSTEM FOR DETECTING COUNTERFEIT GOODS AND METHOD OF OPERATING THE SAME

BACKGROUND

The embodiments described herein relate generally to a system that employs an x-ray imaging system and, more particularly, to a container handling system that distinguishes containers and objects therein as either originals or counterfeits.

Many known supply-chain merchandise systems process a large number of packages annually, i.e., numbering in some cases in the millions. Typically, there are a number of transfer points for the packages, e.g., loading and unloading points for aircraft transport, sea-based transport, and land-based transport. Also, many transfer points include temporary storage for the packages while awaiting the next mode of transport to receive the packages. As such, any one package may change hands a number of times as it is transported from its origin to its final destination, and a number of opportunities for substitution of original items with counterfeit items is presented. Such items include, but are not limited to, pharmaceuticals, consumer goods, luxury items, and perfumes. For the particular case of counterfeit pharmaceuticals, there is additionally a substantial health risk with medicines that are either ineffective or poisonous.

Many known x-ray transmission techniques, based on object density, are often used to identify counterfeit products. Such x-ray techniques however reveal only 2 dimensions of density information, namely, 2-D spatial projection coordinates. Therefore, while some physical anomalies associated with, e.g., wire bond and missing die in electronic components are detectable, pharmaceutical analyses are more complicated. Some known x-ray powder diffraction (XRPD) systems are used for screening drugs. However, because in some instances, the small samples of substances of interest are ground into powder, and the associated detection system may not pinpoint the location of the suspect materials within a large package or suitcase. As such, opening of the suitcase or package for a manual inspection will be necessitated, and the screening process may take an extended period of time, i.e., hours, thereby limiting the potential for such XRPD systems to screen a large number of packages with a throughput that facilitates large-scale and expeditious shipping.

BRIEF DESCRIPTION

In one aspect, a computer-implemented method of handling a container including at least one object therein is provided. The method includes performing a first scan of the container including irradiating the container with polychromatic x-rays with a first x-ray scanning system at a first geographic location. The method also includes generating, using the at least one processing device, a first scan record, and then moving the container from the first geographic location to a second geographic location. The method further includes performing a second scan of the container including irradiating the container with polychromatic x-rays with a second x-ray scanning system at the second geographic location and then generating, using the at least one processing device, a second scan record. The method also includes comparing the first scan record and the second scan record and determining whether the second scan record is substantially indistinguishable from the first scan record or the second scan record is substantially distinguishable from the first scan record.

In another aspect, a container handling system is provided. The system includes at least one processing device and a first x-ray scanning system at a first geographic location coupled to the at least one processing device. The first x-ray scanning system is configured to perform a first x-ray scan of a container. The at least one processing device is configured to generate a first scan record of the container. The system also includes a second x-ray scanning system at a second geographic location coupled to the at least one processing device. The second x-ray scanning system is configured to perform a second x-ray scan of the container. The at least one processing device is further configured to generate a second scan record of the container and compare the first scan record and the second scan record. The at least one processing device is further configured to determine whether the container scanned at the second geographic location is substantially indistinguishable from the container scanned at the first geographic location or the container scanned at the second geographic location is distinguishable from the container scanned at the first geographic location.

DRAWINGS

FIG. 1 is a schematic view of an exemplary x-ray diffraction imaging (XDI) system in an X-Y plane;

FIG. 2 is a schematic side view of the x-ray diffraction imaging (XDI) system shown in FIG. 1;

FIG. 3 is a schematic perspective view of an exemplary computed tomography (CT) imaging system;

FIG. 4 is a schematic diagram of the CT imaging system shown in FIG. 3;

FIG. 5 is a schematic diagram of an exemplary detector array that may be used with the CT imaging system shown in FIGS. 3 and 4;

FIG. 6 is a schematic diagram of an exemplary container handling system including one of the XDI system shown in FIG. 1 and the CT imaging system shown in FIGS. 3-5;

Figure 1:
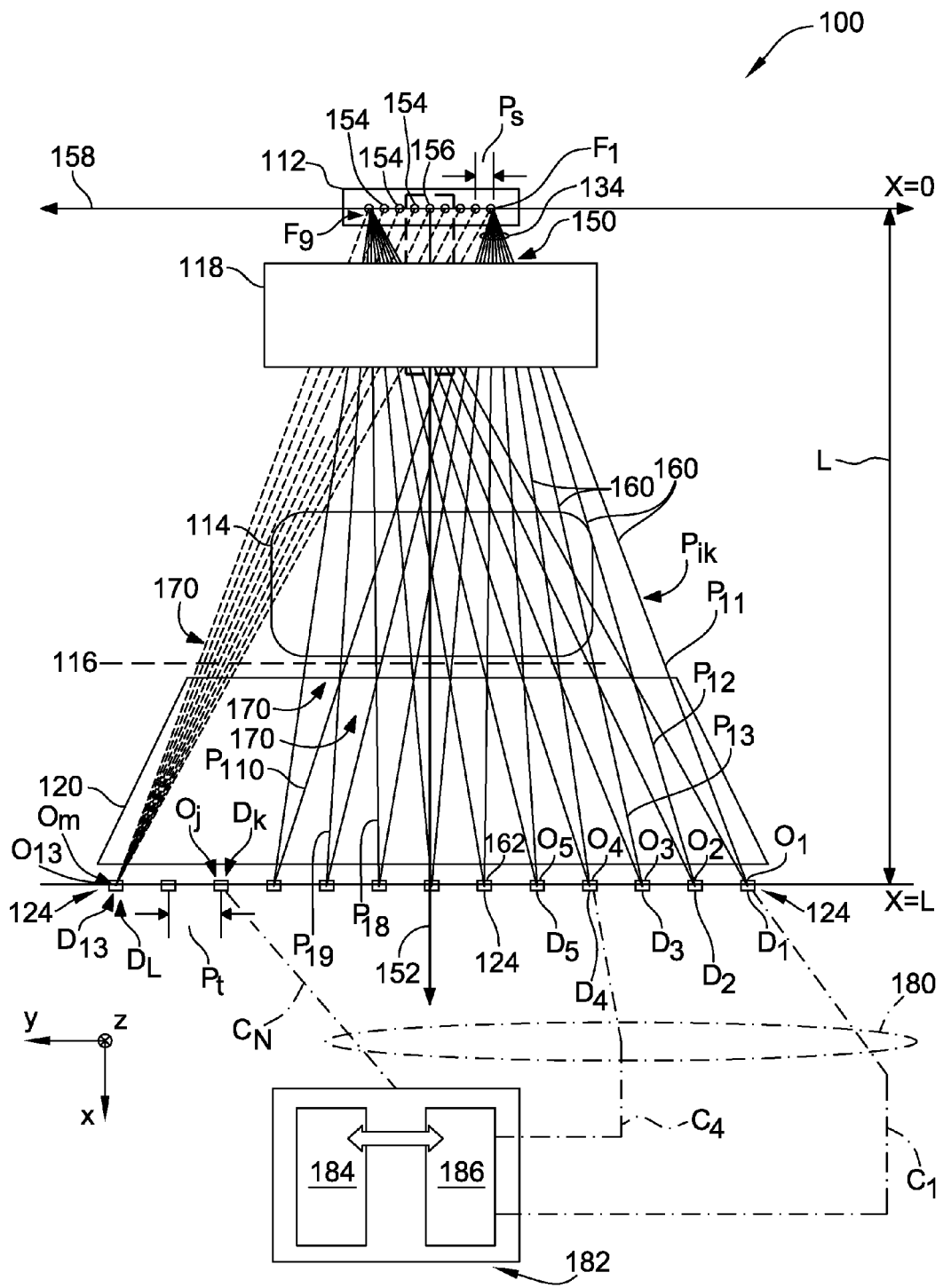
FIGS. 1-8 show exemplary embodiments of the systems and methods described herein.
Figure 4:
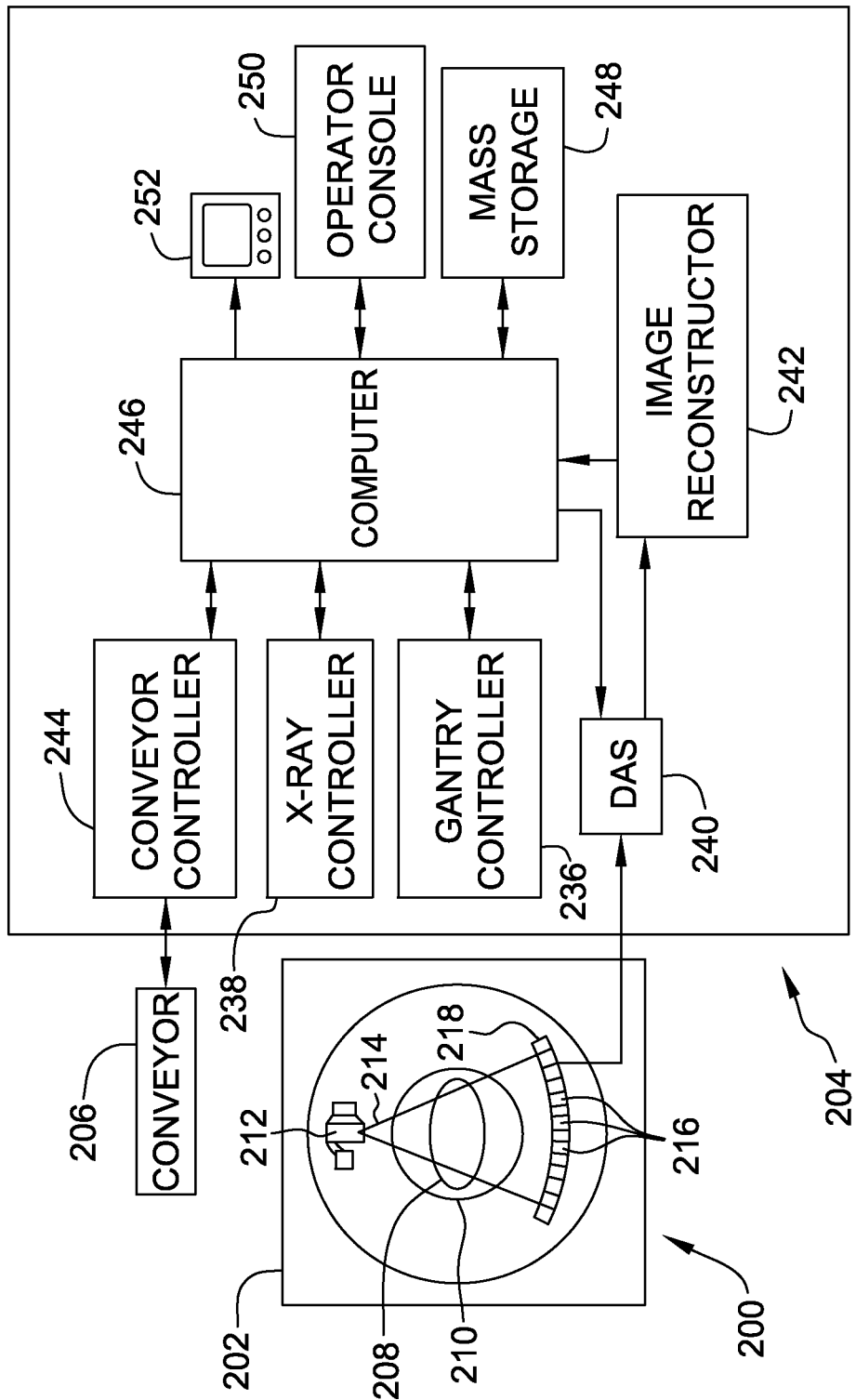
Figure 6:
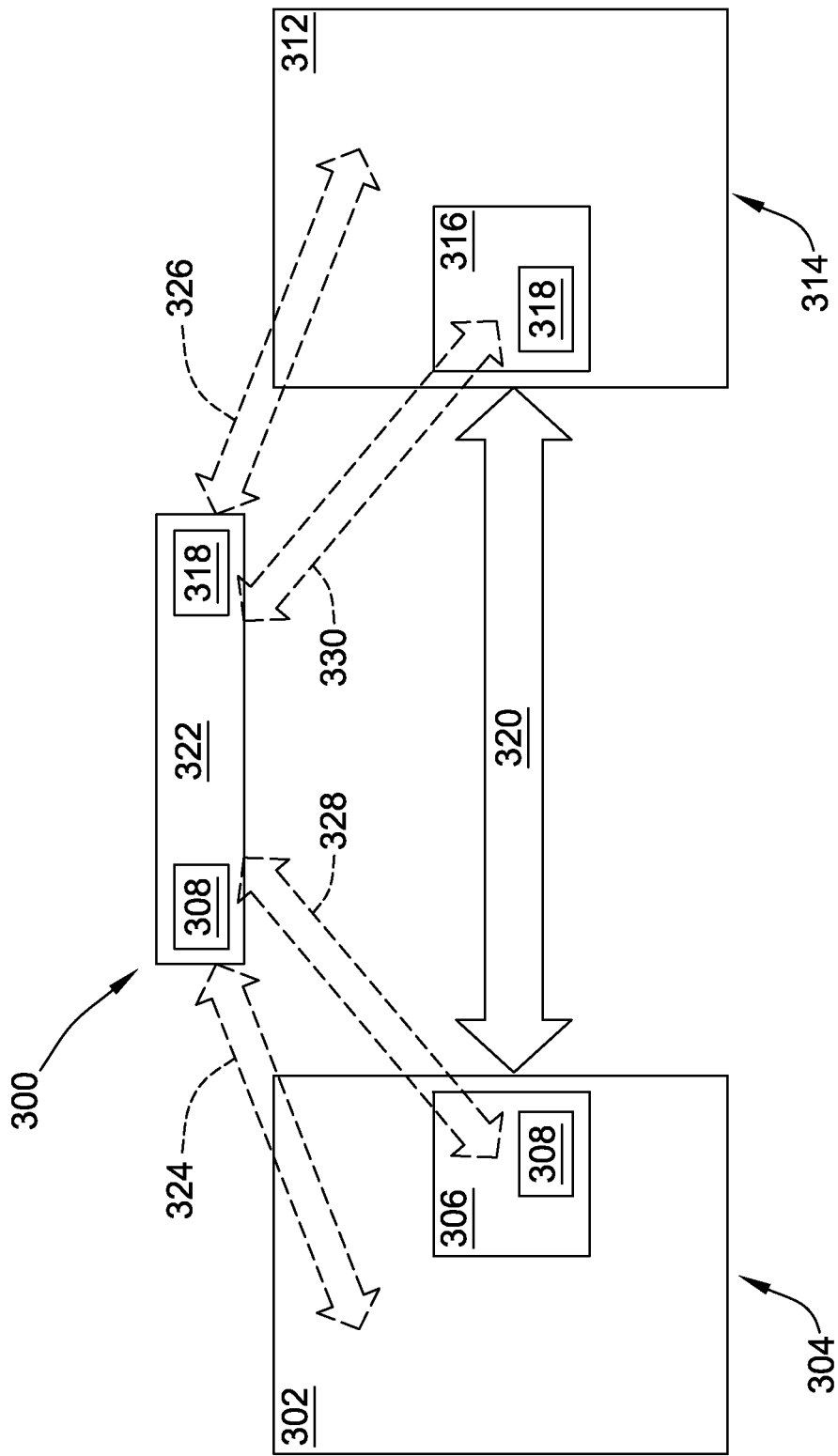
Figure 7:
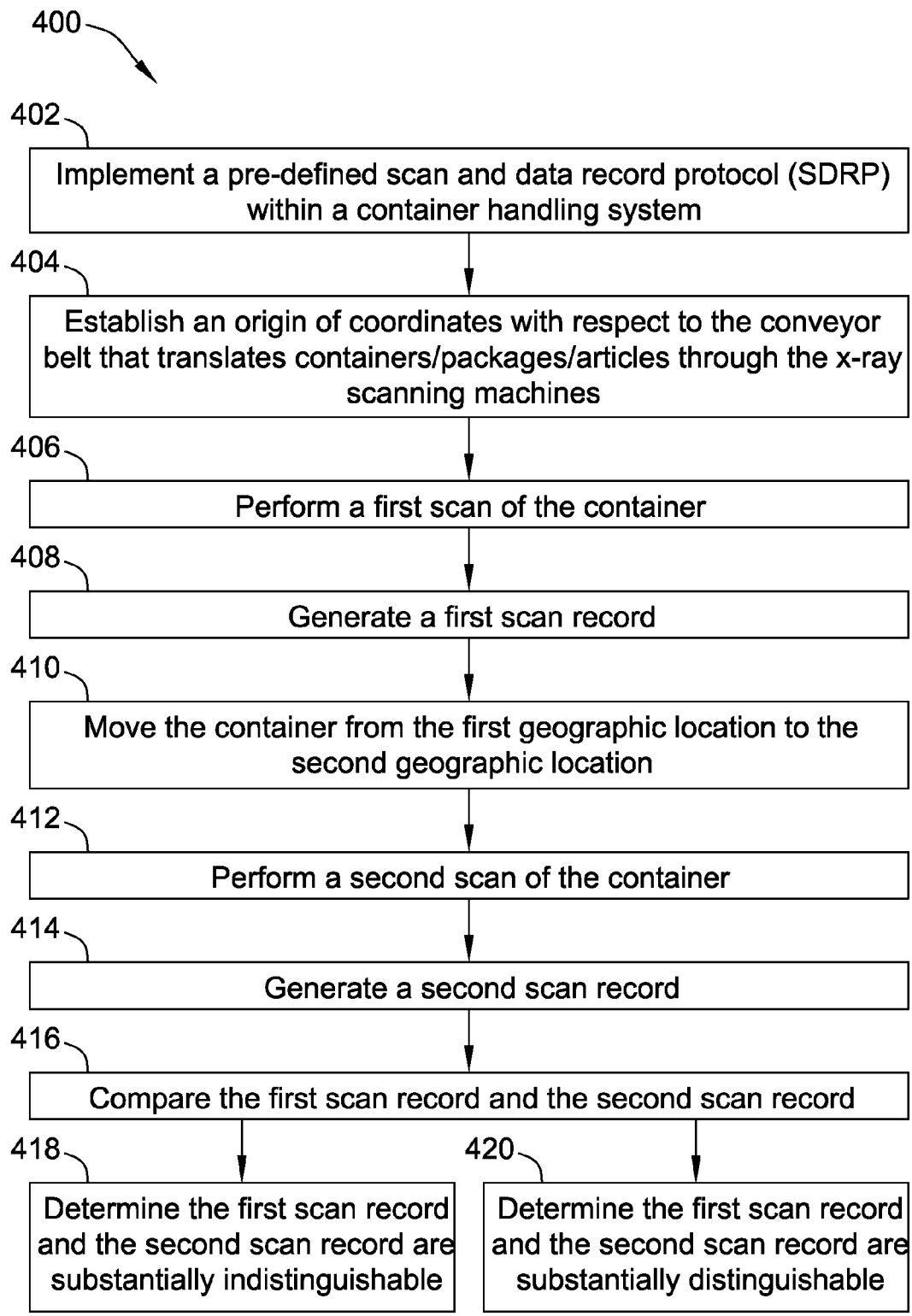
Figure 8:
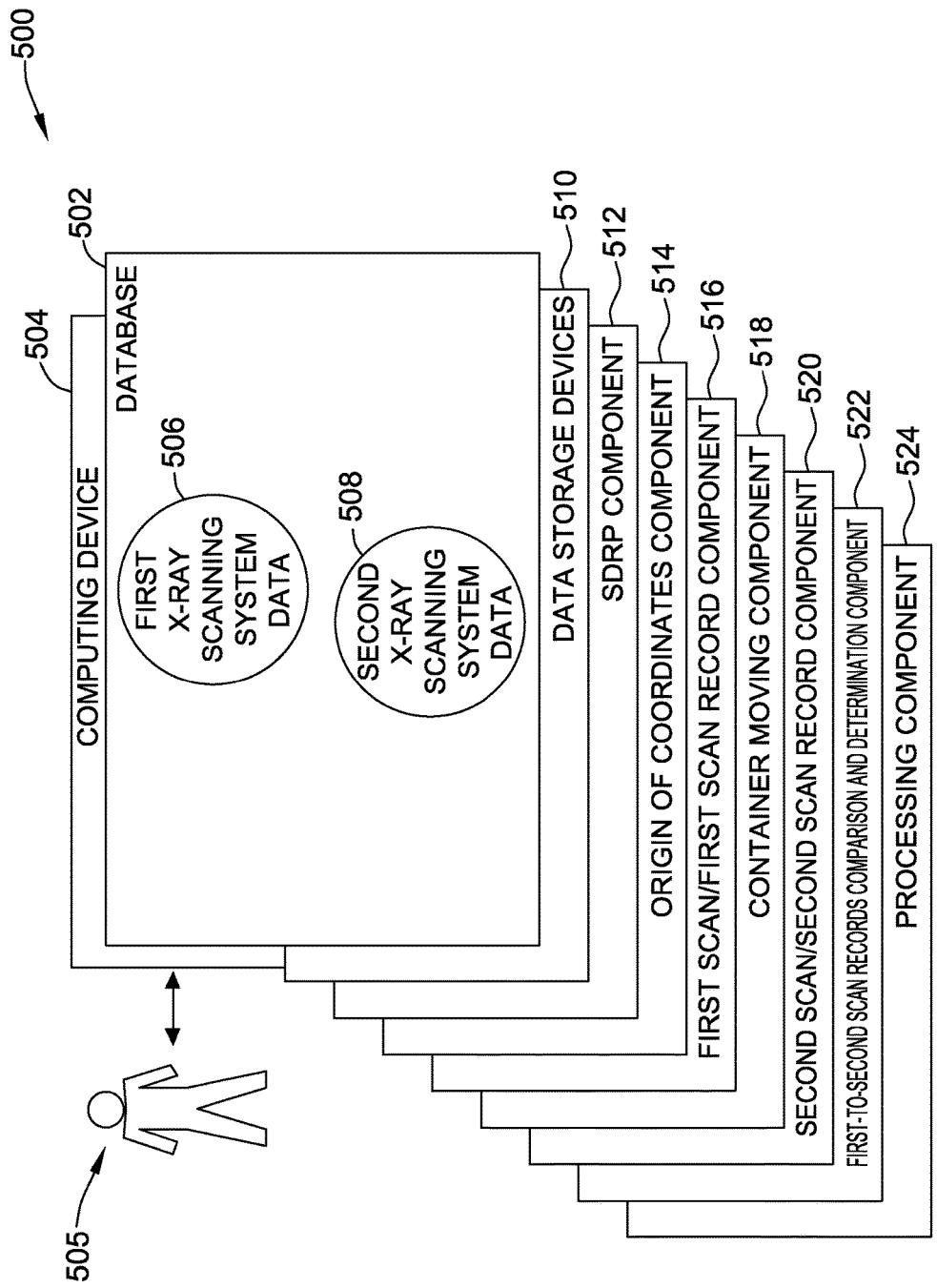

FIG. 7 is a schematic flowchart of an exemplary method of handling a container including at least one object therein using the container handling system shown in FIG. 6; and FIG. 8 is an exemplary configuration of a database within the computing devices shown in FIGS. 1 and 4, along with other related computing components, which may be used to perform a security inspection of a container with the container handling system as described herein.

DETAILED DESCRIPTION

The container handling systems described herein facilitate cost-effective enhanced identification of counterfeit articles with a suitably high probability of detection ($P_D$) and low probability of false alarm, i.e., false positive ($P_{FA}$). Specifically, in contrast to many known x-ray scanning systems, the container handling systems as described herein facilitate distinguishing counterfeit products from authentic products with throughput that facilitates the pace of, e.g., cabin baggage screening (CBS) and hold baggage screening (HBS). More specifically, some of the container handling systems as described herein use multidimensional, i.e., four-dimensional (4-D) screening, i.e., three orthogonal spatial dimensions and an energy dimension using a computed tomography (CT) imaging system to screen the articles.

Further, some of the container handling systems as described herein use multidimensional, i.e., five-dimensional (5-D) screening, i.e., three orthogonal spatial dimensions, a momentum dimension, and an angle of incidence dimension, using an x-ray diffraction imaging (XDI) system to screen the articles. A particular authentic package is scanned at it leaves, e.g., a production facility, in a pre-defined orientation and with a pre-defined scan and data record protocol (SDRP) using an XDI screener e.g., a CBS or a HBS, or a CT imaging system. A record is made of the multidimensional dependence of detector signals from this package. An arrangement is implemented to ensure that the same package is re-scanned at the point-of-sale or its receipt by the end user using the same orientation with which the package was originally scanned. The two sets of scanned multidimensional data are compared to authenticate the received package as the original package or not.

FIG. 1 is a schematic view of an exemplary x-ray diffraction imaging (XDI) system 100 in an X-Y plane. In the exemplary embodiment, XDI system 100 is a multi-detector inverse fan beam x-ray diffraction imaging (MIFB XDI) system. Alternatively, system 100 is any XDI system that enables operation of system 100 as described herein. XDI system 100 includes a multi-focus x-ray source (MFXS) 112, an examination area 114, a support 116 configured to support a container, a primary collimator 118, and a secondary collimator 120. XDI system 100 also includes two types of detectors, an array of transmission detectors (not shown) and a plurality of discrete coherent x-ray scatter detectors 124, which are energy-resolving photon counting detectors. The transmission detectors are offset in a z-axis direction from coherent x-ray scatter detectors 124.

Examination area 114, i.e., the baggage tunnel through which the conveyor belt moves of an XDI-type CBS is approximately 60 cm wide in the Y-dimension by approximately 40 cm high in the X-dimension. The examination area 114 of an XDI-type HBS is approximately 100 cm wide in the Y-dimension by approximately 60 cm high in the X-dimension. Both the CBS and HBS XDI screeners employ the same multi-detector inverse fan beam (MIFB) topology. The choice of whether to use a CBS or HBS XDI screener depends on the size of the package to be investigated. The package to be screened is supported on a conveyor belt, which transports the object through the active region of the XDI screener. The length of the package is unlimited in the direction of conveyor belt motion, i.e., the Z-dimension.

In the exemplary embodiment, MFXS 112 is configured to emit polychromatic x-ray radiation sequentially from a plurality of focus points, as described below, distributed along MFXS 112 in a direction substantially parallel to a y-axis perpendicular to the z-axis. In the exemplary embodiment, MFXS 112 has nine (9) focus points. In alternative embodiments, MFXS 112 has approximately 40 to 100 focus points. Also alternatively, MFXS 112 may include any suitable number of focus points that enables operation of XDI system 100 as described herein.

Further, in the exemplary embodiment, MFXS 112 is located on or coupled to an upper support surface, such as at or near a ceiling, while the transmission detectors and coherent x-ray scatter detectors 124 are located on, or coupled to, a lower support structure, such as at or near a floor. In an alternative embodiment, MFXS 112 is located on or coupled to a lower support structure, such as at or near a floor, while the transmission detectors and coherent x-ray scatter detectors 124 are located on or coupled to an upper support surface, such as at or near a ceiling. Further, in the exemplary embodiment, MFXS 112, the transmission detectors and coherent x-ray scatter detectors 124 are stationary, support 116 is a conveyor belt capable of translation backward and forward in a direction substantially parallel to the z-axis, and examination area 114 is a baggage tunnel through which the conveyor belt moves. In an alternative embodiment, MFXS 112, the transmission detectors and coherent x-ray scatter detectors 124 are capable of coordinated movement at least in a direction substantially parallel to the z-axis, and support 116 is stationary. In certain alternative embodiments, MFXS 112, the transmission detectors, coherent x-ray scatter detectors 124, and support 116 are all capable of movement.

In the exemplary embodiment, MFXS 112 is configured to emit, through primary collimator 118, a set of polychromatic x-ray pencil beams 134, from each focus point of MFXS 112. A portion of the polychromatic x-ray radiation from each pencil beam 134 typically is scattered in various directions upon contact with a container (not shown) in examination area 114. Secondary collimator 120 is configured to facilitate ensuring that a portion of scattered radiation (not shown) arriving at each coherent x-ray scatter detector 124 has a constant scatter angle with respect to the corresponding pencil beam 134 from which the scattered radiation originated. The polychromatic x-ray radiation for each pencil beam 134 is generated through an x-ray tube (not shown) that includes an anode (discussed further below) and a cathode (e.g., and without limitation, tungsten filament) coupled to an electric power source (not shown) that receives a voltage and a current that is controlled by a processing device (discussed further below).

In the exemplary embodiment, a multi-detector inverse fan beam 150 formed from a set of polychromatic x-ray pencil beams 134 is projected along x-axis 152 onto the X-Y plane. More specifically, pencil beams 134 of fan beam 150 fan out in the X-Y plane. Pencil beams 134 of fan beam 150 also fan out in the X-Z plane. In one embodiment, MFXS 112 emits radiation sequentially from a plurality of focus points 154. More specifically, MFXS 112 includes an anode 156 and a plurality of focus points 154 arranged along a length of anode 156 collinear with a y-axis 158 of MFXS 112. Each focus point 154 is sequentially activated to emit an x-ray fan beam. For example, a focus point $F_1$ emits MIFB fan beam 150 that extends between and is detected by coherent x-ray scatter detector $D_1$ through and including coherent x-ray scatter detector $D_{13}$ and includes a plurality of pencil primary beams 160. Focus points 154 are denoted $F_1, F_2, \ldots F_i, \ldots F_n$ with a running index i. Primary collimator 118 is configured to select from the radiation emitted at each focus point 154, primary beams that are directed to a series of convergence points 162 labeled $O_1, O_2, \ldots, O_j, \ldots O_m$ with a running index j regardless of which focus point 154 is activated. Ten primary beams 160 are shown in FIG. 1 with each primary beam 160 emitted from focus point $F_1$ directed to a corresponding convergence point $O_1, O_2, \ldots, O_j, \ldots O_{13}$ positioned along a line parallel to y-axis 158 at a coordinate X=L with focus point $F_1$ activated.

A plurality of discrete coherent x-ray scatter detectors 124 labeled discrete coherent x-ray scatter detectors $D_1, D_2, \ldots D_k, \ldots D_L$ with a running index k are positioned at a suitable or desirable distance in a direction along the Z-axis from a corresponding convergence point 162 to record coherent scatter from primary beam $P_{ij}$ in discrete coherent x-ray scatter detector $D_k$. A combination of MFXS 112 and discrete coherent x-ray scatter detectors 124 facilitates examining a volume of a container positioned within examination area 114 without any dead area from which no XDI signal is detected or measured.

As primary beams 160 labeled $P_{ij}$ propagate through a container (not shown) positioned within examination area 114, primary beam $P_{ij}$ interacts with the container to produce coherent scatter that may be detected in coherent x-ray scatter detectors $D_{j+1}$, $D_{j+2}$, $D_{j-1}$, and/or $D_{j-2}$, for example. Primary beams $P_{11}$, $P_{12}$, $P_{13}$, $P_{14}$, $P_{15}$, ... $P_{1k}$, ... $P_{1L}$, are emitted from focus point $F_1$ and directed to corresponding convergence points $O_1$, $O_2$, $O_3$, $O_4$, $O_5$, ..., $O_j$, ... $O_m$, respectively. As each primary beam $P_{11}$, $P_{12}$, $P_{13}$, $P_{14}$, $P_{15}$, ... $P_{1k}$, ... $P_{1L}$ moves through examination area 114, each primary beam $P_{11}$, $P_{12}$, $P_{13}$, $P_{14}$, $P_{15}$, ... $P_{1k}$, ... $P_{1L}$ collides with and/or interacts with a container (not shown) positioned within examination area 114 to produce coherent scatter (not shown) that is detectable at one or more coherent x-ray scatter detectors $D_1$, $D_2$, $D_3$, $D_4$, $D_5$, ... $D_k$, ... $D_L$ for example.

In the exemplary embodiment, MFXS 112 is positioned on the y-axis (x=0) of a Cartesian coordinate system. Each focus point 154 has a position on a grid having a pitch, $P_s$. Further, convergence points 162 lie parallel to the y-axis at coordinate X=L, and each convergence point 162 has a position on a grid having a pitch, $P_t$. In a particular embodiment, for an XDI checked baggage screening system, L has a value of about 2000 millimeters (mm), $P_s$ has a value of about 20 mm, and $P_t$ has a value of about 200 mm. Alternatively, L, $P_s$ and $P_t$ have any values that enable operation of XDI system 100 as described herein.

A plurality of coherent x-ray scatter detectors 124 are positioned at the same y-coordinate as convergence points 162. One pair of coherent x-ray scatter detectors 124 may be associated with a corresponding convergence point 162 with the pair of coherent x-ray scatter detectors 124 positioned on both sides of the X-Y plane. In a further embodiment, thirteen (13) convergence points are used to allow for several convergence point position arrangements to incorporate a different number of coherent x-ray scatter detectors 124. Alternatively, any number of coherent x-ray scatter detectors 124 are used and any number of convergence points are defined within XDI system 100 that enables operation of XDI system 100 as described herein, including, without limitation, seventeen (17) detectors 124 and convergence points.

If all convergence points 162 have detector pairs then XDI system 100 may include twenty-six (26) coherent x-ray scatter detectors 124. In alternative embodiments, fewer coherent x-ray scatter detectors 124 may be positioned at convergence point positions 1, 3, 5, 7, 9, 11, and 13, at convergence point positions 1, 4, 7, 10, and 13, or at convergence point positions 1, 5, 9, and 13 to account for manufacturing and/or cost constraints.

A left-most detector D13 detects a plurality of primary beams 160 labeled $P_{113}$, $P_{213}$, ... $P_{ik}$, ... $P_{913}$, alternatively referred to herein as an inverse fan beam bundle 170 of primary beams, from each focus point 154 denoted $F_1$, $F_2$, ... $F_i$, ... $F_9$ of MFXS 112 that are transmitted by primary collimator 118. Inverse fan beam bundle 170 is significantly narrower than a width of examination area 114. MFXS 112, as depicted in FIG. 1 is not shown to scale for clarity's sake, and may be smaller than shown. Moreover, only 13 convergence points 162 are shown although, as described above, in practice the number of convergence points 162 can be much greater. Further, the scatter signal is proportional to a number of coherent x-ray scatter detectors 124 incorporated into XDI system 100.

Several inverse fan beam bundles 170 of primary beams directed towards a corresponding convergence point $O_j$ are detected by a corresponding coherent x-ray scatter detector $D_k$. During a scan of the container positioned within examination area 114, during which each focus point 154 of MFXS 112 is sequentially activated, the container section is completely irradiated and scatter signals are measured from an entire width of the container. In this embodiment, no mechanical movements are required to achieve a complete 2-D and/or 3-D scan of the container. MFXS 112 achieves this with only a small x-ray source dimension along the y-axis. In the exemplary embodiment, MFXS 112 has a length along the y-axis of less than about 500 mm. A small x-ray source dimension is advantageous from the viewpoints of cost and reliability.

As described above, XDI system 100 includes two types of detectors, i.e., an array of transmission detectors (not shown) and a plurality of discrete coherent x-ray scatter detectors 124, each individually labeled as $D_1$, $D_2$, $D_3$, $D_4$, $D_5$, ... $D_k$, ... $D_L$. The transmission detectors are offset in the z-axis direction from coherent x-ray scatter detectors 124. In the exemplary embodiment, the transmission detectors are charge integration detectors, while coherent x-ray scatter detectors 124 are pulse-counting energy-resolving detectors. The transmission detectors and each coherent x-ray scatter detector 124 are in electronic communication with a number of channels 180, for example, N number of channels $C_1$, ... $C_p$, ... $C_N$, with a running index p where N is selected based on the configuration of XDI system 100, and where only those channels C associated with coherent x-ray scatter detectors 124 are shown. Channels 180 electronically communicate data collected by the transmission detectors and each coherent x-ray scatter detector 124 to a computing device 182. In the exemplary embodiment, computing device 182 combines an output from the transmission detectors and an output from coherent x-ray scatter detectors 124 to generate information about the contents of a container positioned within examination area 114. For example, but not by way of limitation, computing device 182 may generate multiview projections and/or section images of a container (not shown) in examination area 114 that identify a location in the container of specific materials detected by XDI analysis.

In the exemplary embodiment, computing device 182 includes a processing device 184 in communication with the transmission detectors and coherent x-ray scatter detectors 124 through a memory device 186. Processing device 184 is programmed, i.e., configured to receive from coherent x-ray scatter detectors 124 output signals representative of the detected x-ray quanta and generate a distribution of momentum transfer values, Q, from a spectrum of energy, E, of x-ray quanta within scattered radiation (not shown) detected by coherent x-ray scatter detectors 124. In some embodiments, processing device 184 is also in communication with, and configured to control, MFXS 112.

As used herein, the terms "processor", "processing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, e.g., firmware, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Also, as used herein, the terms "software" and "firmware" are interchangeable, and include any computer program stored in memory for execution by personal computers, workstations, clients and servers.

Further, as used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Processing device 184 and other processors (not shown) as described herein process information transmitted from a plurality of electrical and electronic devices that include, without limitation, coherent x-ray scatter detectors 124. Memory devices 186 and storage devices (not shown) store and transfer information and instructions to be executed by processing device 184. Such memory devices 186 and storage devices can also be used to store and provide temporary variables, static (i.e., non-volatile and non-changing) information and instructions, or other intermediate information to processing device 184 during execution of instructions by processing device 184. Instructions that are executed include, but are not limited to, analysis of signals transmitted from coherent x-ray scatter detectors 124. The execution of sequences of instructions is not limited to any specific combination of hardware circuitry and software instructions.

Figure 2:
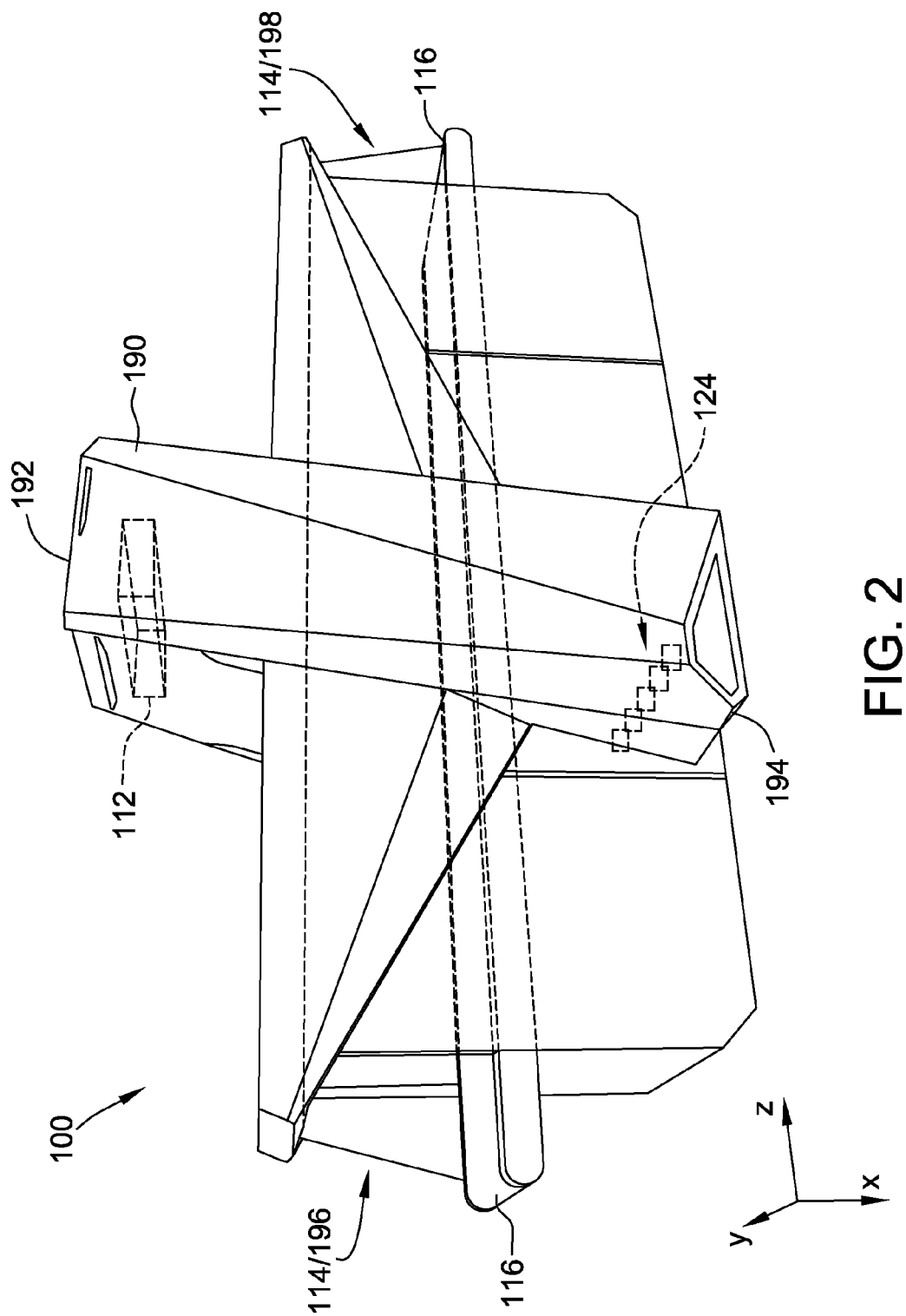

FIG. 2 is a schematic side view of XDI system 100 as implemented and deployed. XDI system 100 includes an external casing 190. As described above, in the exemplary embodiment, MFXS 112 (shown in phantom) is located on, or coupled to, an upper support surface 192 of casing 190. The transmission detectors and coherent x-ray scatter detectors 124 (shown in phantom) are located on, or coupled to, a lower support surface 194. Support 116 is a conveyor belt capable of translation backward and forward in a direction substantially parallel to the z-axis, and examination area 114 is a baggage tunnel through which the conveyor belt moves. Examination area 114 is at least partially defined by an inlet end 196 and an outlet end 198.

Figure 3:
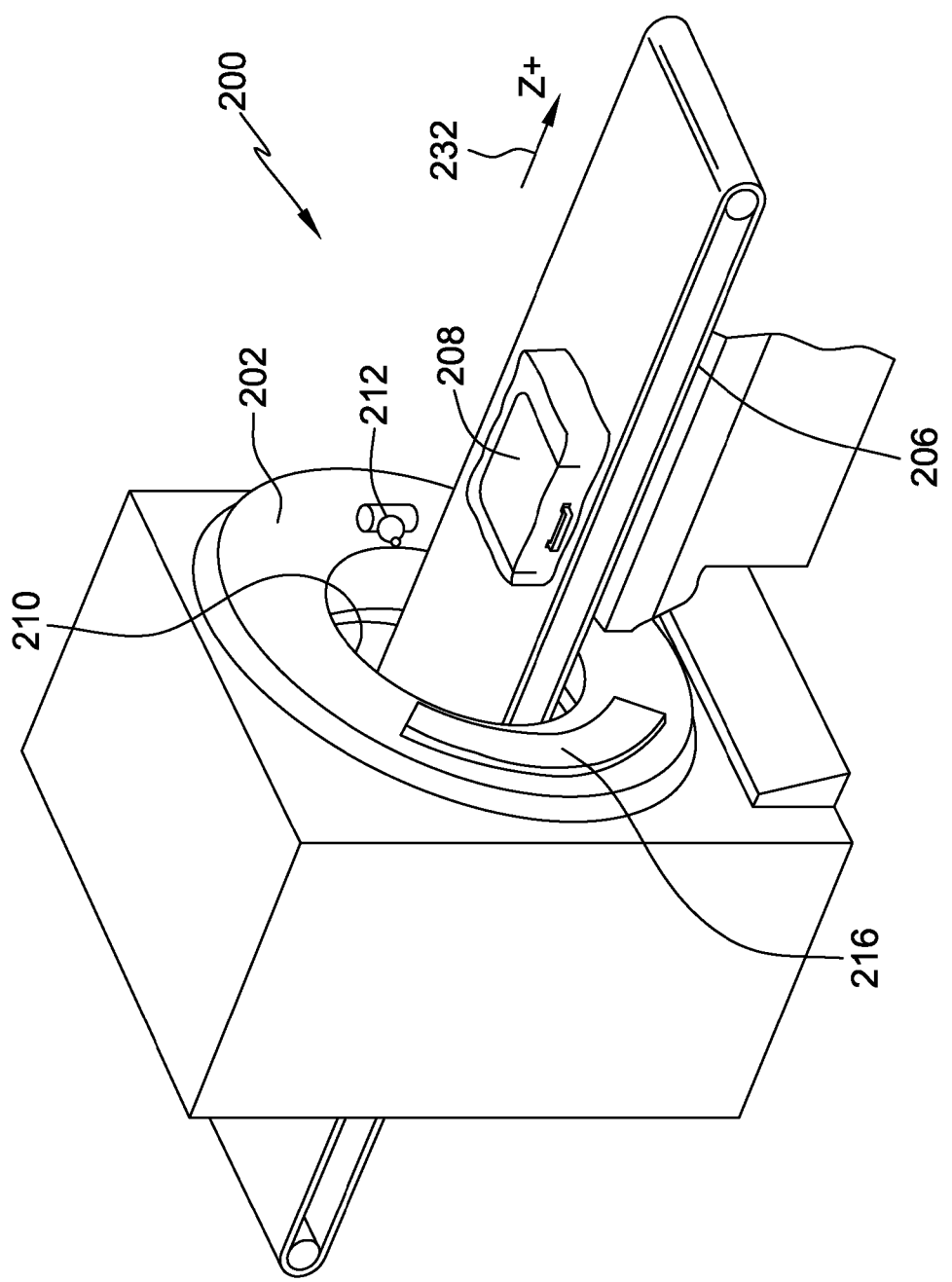

FIG. 3 is a schematic perspective view of an exemplary computed tomography (CT) imaging system 200. FIG. 4 is a schematic diagram of CT imaging system 200. Referring to FIGS. 3 and 4, CT imaging system 200 is shown having a gantry 202, which is representative of a CT scanner, a control system 204, and a motorized conveyor belt 206 for positioning a container 208, such as a piece of luggage or a shipping container or package, in a gantry opening 210 defined through gantry 202. Gantry 202 includes an x-ray source 212 that projects a fan beam of polychromatic x-rays 214 toward a detector array 216 on the opposite side of gantry 202. X-ray source 212 includes an x-ray tube (not shown) that includes and anode and a cathode (e.g., without limitation, tungsten filament) (neither shown) coupled to an electric power source (not shown) that receives a voltage and a current that is controlled by a processing device (described further below).

Detector array 216 is formed by detector elements 218, which are shown in more detail in FIG. 5 and discussed below. Detector elements 218 are radiation detectors that each produce a signal having a magnitude that represents and is dependent on the intensity of the attenuated x-ray beam after it has passed through container 208 being imaged. During a helical scan that acquires x-ray projection data, gantry 202 along with x-ray source 212 and detector array 216 rotate within a plane and around container 208 about a center of rotation, while container 208 is moved through gantry 202 in a z-direction 232 perpendicular to the plane of rotation. In the exemplary embodiment, detector array 216 includes a plurality of detector rings each having a plurality of detector elements 218, the detector rings having an angular configuration corresponding to x-ray source 212.

Gantry 202 and x-ray source 212 are controlled by control system 204, which includes a gantry controller 236, an x-ray controller 238, a data acquisition system (DAS) 240, an image reconstructor 242, a conveyor controller 244, a computer 246, a mass storage-system 248, an operator console 250, and a display device 252. Gantry controller 236 controls the rotational speed and position of gantry 202, while x-ray controller 238 provides power and timing signals to x-ray source 212, and data acquisition system 240 acquires analog data from detector elements 218 and converts the data to digital form for subsequent processing. Image reconstructor 242 receives the digitized x-ray data from data acquisition system 240 and performs an image reconstruction process that involves filtering the projection data using a helical reconstruction algorithm.

Computer 246 is in communication with gantry controller 236, x-ray controller 238, and conveyor controller 244 whereby control signals are sent from computer 246 to controllers 236, 238, 244 and information is received from controllers 236, 238, 244 by computer 246. Computer 246 also provides commands and operational parameters to data acquisition system 240 and receives reconstructed image data from image reconstructor 242. The reconstructed image data is stored by computer 246 in mass storage system 248 for subsequent retrieval. An operator interfaces with computer 246 through operator console 250, which may include, for example, a keyboard and a graphical pointing device, and receives output, such as, for example, a reconstructed image, control settings and other information, on display device 252.

Communication between the various system elements of FIG. 4 is depicted by arrowhead lines, which illustrate a means for either signal communication or mechanical operation, depending on the system element involved. Communication amongst and between the various system elements may be obtained through a hardwired or a wireless arrangement. Computer 246 may be a standalone computer or a network computer and may include instructions in a variety of computer languages for use on a variety of computer platforms and under a variety of operating systems. Other examples of computer 246 include a system having a microprocessor, microcontroller or other equivalent processing device capable of executing commands of computer readable data or program for executing a control algorithm. In order to perform the prescribed functions and desired processing, as well as the associated computations, e.g., the execution of fourier analysis algorithm(s) and the control processes prescribed herein, computer 246 includes, without limitation to, a processor(s), memory, storage, register(s), timing, interrupt(s), communication interfaces, and input/output signal interfaces, as well as combinations including at least one of the foregoing. For example, computer 246 may include input signal filtering to enable accurate sampling and conversion or acquisitions of such signals from communications interfaces. As described above, exemplary embodiments can be implemented through computer-implemented processes and apparatuses for practicing those processes.

Figure 5:
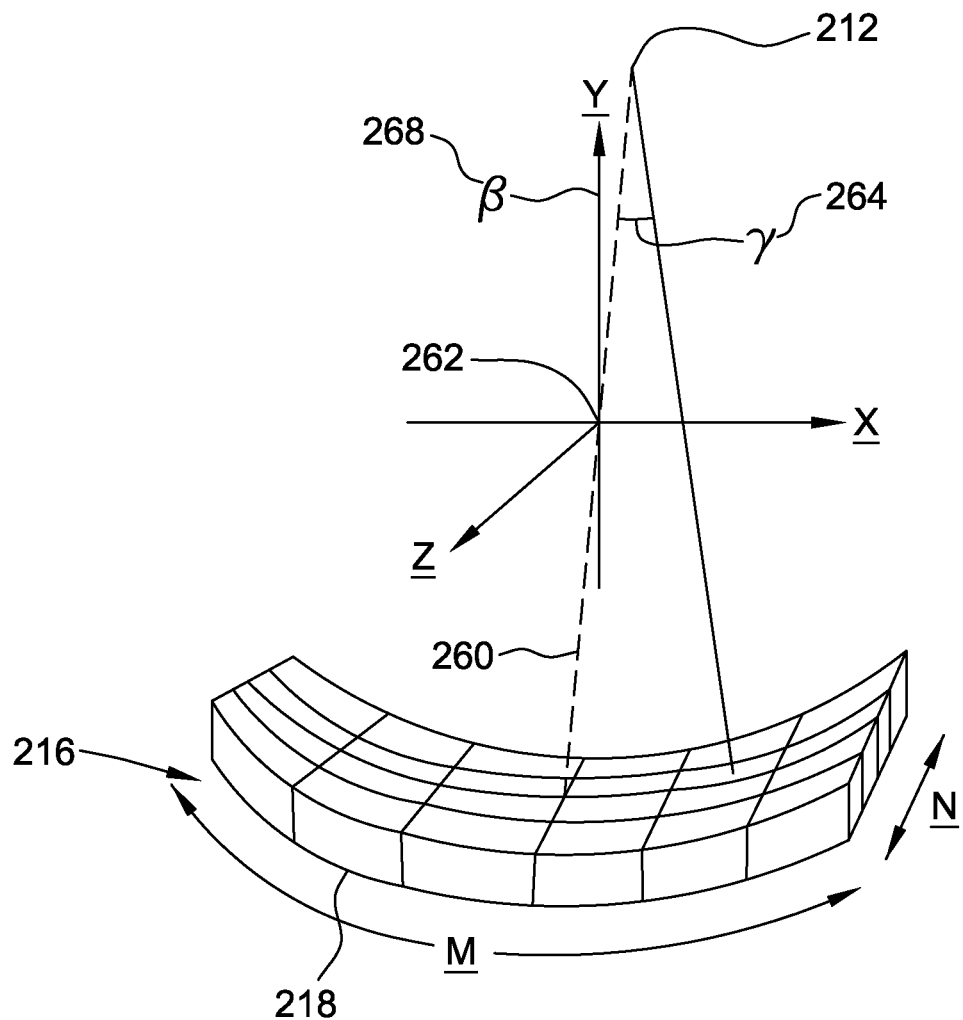

FIG. 5 is a schematic diagram of detector array 216 that may be used with CT imaging system 200 (shown in FIGS. 3 and 4). An x-ray beam includes a beam axis (iso-ray) 260 that originates at x-ray source 212 and passes through center of rotation (iso-center) 262, relative to detector array 216, having detector elements 218 arranged in rows N and columns M, is provided. While FIG. 4 depicts only four rows (N=4 for four rings) and six columns (M=6 for six detectors per ring), any number of rows and columns may be employed as a matter of design choice. For example, some embodiments includes from sixteen to thirty-two rows of detector elements 218. Detector rows and detector rings are used interchangeably herein. As depicted in FIG. 4, a detector angle γ 264 is shown as an angle formed between an x-ray intersecting a given detector element 218 and iso-ray 260 which connects x-ray source 212 and the iso-center 262, and a projection angle β 268 is shown as an angle formed by iso-ray 260 with the y-axis.

FIG. 6 is a schematic diagram of an exemplary container handling system 300 including one of XDI system 100 (shown in FIG. 1) and CT imaging system 200 (shown in FIGS. 3-5). In the exemplary embodiment, container handling system 300 is a part of a broader shipping/transport system. Alternatively, container handling system 300 is part of an inventory management system for a facility, including, and without limitation, a storage facility. Further, alternatively, container handling system 300 is a system for any facility and for any process that has reason to verify container 208 and the contents therein are the authorized versions and are not unauthorized substitutes.

Container handling system 300 includes a first x-ray scanning system 302 at a first geographic location 304. First x-ray scanning system 302 includes a first processing device 306. In operation, first x-ray scanning system 302 performs a first x-ray scan of container 208 (shown in FIGS. 3 and 4) and first processing device 306 generates a first scan record 308 of container 208. Container handling system 300 also includes a second x-ray scanning system 312 at a second geographic location 314. Second x-ray scanning system 312 includes a second processing device 316. In operation, second x-ray scanning system 312 performs a second x-ray scan of container 208 and second processing device 316 generates a second scan record 318 of container 208. In the exemplary embodiment, processing devices 306 and 316 are in bi-directional communication as indicated by double-headed arrow 320. As such, processing devices 306 and 316 generate commands and receive operational data in a manner similar to processing device 184 (shown in FIG. 1) for XDI-type systems. Similarly, for CT-type imaging systems, processing devices 306 and 316 generate commands and receive operational data in a manner similar to any combination of control system 204, gantry controller 236, x-ray controller 238, conveyor controller 244, image reconstructor 242, and computer 246 (all shown in FIG. 4).

Alternatively, in some embodiments, a single third processing device 322 (shown in phantom) is coupled to each of first x-ray scanning system 302 and second x-ray scanning system 312. In such embodiments, x-ray scanning systems 302 and 312 are in bi-directional communication with third processing device 322 as indicated by double-headed phantom arrows 324 and 326, respectively. Also, in such embodiments, first processing device 306 and second processing device 316 are replaced with third processing device 322 and device 322 performs substantially all of the functions of processing devices 306 and 316.

Also, alternatively, in some embodiments, third processing device 322 is coupled to each of first processing device 306 and second processing device 316. In such embodiments, the features described herein for imaging system control and data manipulation and management are distributed between processing devices 306, 316, and 322 in any manner that enables operation of container handling system 300. Also, in such embodiments, first processing device 306 and second processing device 316 are in bi-directional communication with third processing device 322 as indicated by double-headed phantom arrows 328 and 330, respectively. Further, alternatively, any number of any type of processing devices in any configuration that enables operation of container handling system 300 as described herein is used.

In the exemplary embodiment, container handling system 300 compares first scan record 308 and second scan record 318 of container 208 and determines if container 208 scanned at second geographic location 314 is substantially indistinguishable from container 208 scanned at first geographic location 304 or if container 208 scanned at second geographic location 314 is distinguishable from container 208 scanned at first geographic location 304. For example, and without limitation, container handling system 300 facilitates determining if a package and its contents shipped from an origin, i.e., first geographic location 304 is the same package and contents arriving at second geographic location 314, or if somewhere in transit between locations 304 and 314, the package or its contents were intercepted and replaced with, for example, counterfeit articles.

Also, in the exemplary embodiment, processing device 306 executes a scan record protocol for performing a first scan of container 208 with first x-ray scanning system 302. The scan record protocol includes predefined parameters for one or more of, and without limitation, a speed of conveyor belt 206 (shown in FIGS. 3 and 4) or support 116 (shown in FIG. 1), a speed distribution along a dimension substantially parallel to a direction of translation of conveyor belt 206 or support 116, a voltage of the x-ray tube, and a current of the x-ray tube. The scan record protocol is applied to first x-ray scanning system 302 during the first scan by first processing device 306. The same scan record protocol is transmitted to second processing device 316 as shown by arrow 320 and second processing device 316 applies the scan record protocol to second x-ray scanning system 312 during the second scan.

Further, in the exemplary embodiment, an origin of coordinates with respect to conveyor belt 206 or support 116 is established and stored within memories and data storage devices for each of first x-ray scanning system 302 and second x-ray scanning system 312 for use by first processing device 306 and second processing device 316, respectfully.

Moreover, in the exemplary embodiment, container handling system 300 includes a data record protocol implemented in first processing device 306 and second processing device 316. The data record protocol is applied to first x-ray scanning system 302 during the first scan and second x-ray scanning system 312 during the second scan. Specifically, the data record protocol is used to reconstruct a first multidimensional, i.e., either a four-dimensional (4-D) or a five-dimensional (5-D) voxelized representation of container 208 using first scan record 308. Also, the data record protocol is used to reconstruct a second multidimensional, i.e., either a 4-D or a 5-D voxelized representation of container 208 using second scan record 318. The first multidimensional voxelized representation of container 208 and the second multidimensional voxelized representation of container 208 each include a plurality of volume elements (voxels). In each of the 4-D voxelized representations, the first three dimensions represent a spatial location of each voxel of the plurality of voxels, and the fourth dimension represents a plurality of energy values defining an energy spectrum of the polychromatic x-rays. In each of the 5-D voxelized representations, the first three dimensions represent a spatial location of each voxel of the 5-D representation, the fourth dimension represents a plurality of momentum transfer values defining a momentum transfer spectrum of container 208, and the fifth dimension represents a plurality of angles of incidence, defined with respect to a system axis, of x-rays irradiating each voxel.

The data record protocol includes, but is not limited to, information such as, and without limitation, predefined parameters regarding voxel aggregation, data correction, and data reduction, i.e., feature extraction. As such, in the exemplary embodiment, container handling system 300, through the data record protocol implemented within first processing device 306 and second processing device 316, aggregates at least a portion of the plurality of voxels in at least one of the first multidimensional voxelized representation of container 208 and the second multidimensional voxelized representation of container 208. Also, container handling system 300, through the data record protocol, corrects at least a portion of data within at least one of first scan record 308 and second scan record 318. Further, container handling system 300, through the data record protocol, extracts at least a portion of data within at least one of first scan record 308 and second scan record 318. In the exemplary embodiment, the scan record protocol and the data record protocol are combined into a pre-defined scan and data record protocol (SDRP). The SDRP is devised and implemented, dependent on the type of container or package to be scanned and the type of contents to be verified, to facilitate increasing the likelihood of detecting counterfeit goods.

FIG. 7 is a schematic flowchart of an exemplary method 400 of handling container 208 (shown in FIGS. 3 and 4) including at least one object therein using container handling system 300 (shown in FIG. 5).

Referring to FIGS. 6 and 7, a pre-defined scan and data record protocol (SDRP) is implemented 402 within container handling system 300. The SDRP is devised to facilitate increasing the likelihood of distinguishing original and counterfeit goods and depends on the package concerned. In the exemplary embodiment, a scan record protocol portion of the SDRP and a data record protocol portion of the SDRP are combined. Each SDRP is based on exhaustive testing and knowledge of the containers and the contents. The SDRP is devised and implemented as a function of the type of container or package to be scanned and the type of contents and objects therein to be verified to facilitate increasing the likelihood of detecting counterfeit goods. As such, a plurality of scan record protocol portions, and therefore, a plurality of SDRPs are implemented within first processing device 306 and second processing device 316 for the known and planned container screening activities. The SDRPs are selected using well-known menu-based features. Alternatively, the SDRPs are selected using any method that enables operation of container handling system 300 as described herein.

The scan record protocol portion includes predefined parameters for one or more of, and without limitation, a speed of conveyor belt 206 (shown in FIGS. 3 and 4) or support 116 (shown in FIG. 1), a speed distribution along a dimension substantially parallel to a direction of translation of conveyor belt 206 or support 116, a voltage of the x-ray tube, and a current of the x-ray tube.

The SDRP also includes the data record protocol portion implemented in first processing device 306 and second processing device 316. The data record protocol portion includes, but is not limited to, information such as, and without limitation, predefined parameters regarding voxel aggregation, data correction, and data reduction, i.e., feature extraction. As described above, the data record protocol portion implemented within first processing device 306 and second processing device 316 aggregates at least a portion of the plurality of voxels in at least one of the first multidimensional voxelized representation of container 208 and the second multidimensional voxelized representation of container 208. Also, the data record protocol portion corrects at least a portion of data within at least one of first scan record 308 and second scan record 318. Further, the data record protocol portion extracts at least a portion of data within at least one of first scan record 308 and second scan record 318.

An origin of coordinates is established 404 in the Y and Z dimensions referred to with respect to support 116 (both shown in FIG. 1) that is a conveyor belt capable of translation backward and forward in a direction substantially parallel to the z-axis (shown in FIG. 1) and motorized conveyor belt 206 capable of translation in a direction substantially parallel to the z-axis (both shown in FIG. 3). This origin of spatial coordinates is realized with e.g., and without limitation, a line drawn on conveyor belt 206 and support 116, subdivided into units of, for example, and without limitation, centimeters (cm). Alternatively the origin of spatial coordinates is realized with a mechanical fixture, for example, and without limitation, a clamp on conveyor belt 206 or support 116, which positions container 208 at a reference location in the Y and Z dimensions. Such origins of coordinates with respect to conveyor belt 206 and support 116 are established and stored within memories and data storage devices for each of first x-ray scanning system 302 and second x-ray scanning system 312 for use by first processing device 306 and second processing device 316, respectfully.

An original, or first scan is performed 406. Immediately before an authentic package, i.e., container 208 leaves, for example, and without limitation, a production facility, container 208 and the contents within are scanned in a pre-defined orientation and with the pre-defined scan and data record protocol (SDRP) using either XDI screening system 100 or CT imaging system 200, e.g., and without limitation, a CBS or a HBS. The contents of container 208 are registered with respect to the place or point of manufacture, for example, and without limitation, a factory. Container 208 is positioned on conveyor belt 206 or support 116 at the origin of coordinates. Container 208 is scanned using parameters contained in the pre-defined SDRP by movement of conveyor belt 206 or support 116 through CT imaging system 200 or XDI system 100, respectively. Container 208 and the articles therein are irradiated with polychromatic x-rays as described for each of systems 100 and 200 as described above. During the first scan, the SDRP is applied to first x-ray scanning system 302 by first processing device 306. The same SDRP is transmitted to second processing device 316 as shown by arrow 320 and second processing device 316 applies the SDRP to second x-ray scanning system 312 during the second scan.

First scan record 308 is generated 408 by first processing device 306. For example, data associated with irradiating container 208 is recorded. Such data includes, for example, in XDI system 100, scattered x-ray signals from respective detectors $D_k$, the value associated with detector line X=L, and the source of the x-rays, i.e., respective focus points $F_j$ (all shown in FIG. 1).

The remainder of the discussion with respect to method 400 describes method 400 using XDI system 100. That is, reconstructing the first multidimensional voxelized representation of container 208 is performed using the first scan record and reconstructing the second multidimensional voxelized representation of container 208 is performed using the second scan record including reconstructing the first and second five-dimensional (5-D) voxelized representations of container 208 using XDI system 100. The first three dimensions represent a spatial location of each voxel of the plurality of voxels, the fourth dimension represents a plurality of momentum transfer values defining a momentum transfer spectrum of container 108, and the fifth dimension represents a plurality of angles of incidence of x-rays irradiating each voxel of the plurality of voxels defined with respect to a system axis.

Alternatively, the remaining method steps of method 400 may also be performed using CT imaging system 200 with the appropriate accommodations. That is, reconstructing the first multidimensional voxelized representation of container 208 is performed using the first scan record and reconstructing the second multidimensional voxelized representation of container 208 is performed using the second scan record including reconstructing a first and second 4-D voxelized representation of container 208 using CT imaging system 200. The first three dimensions represent a spatial location of each voxel of the plurality of voxels, and the fourth dimension represents a plurality of energy values defining an energy spectrum of the polychromatic x-rays.

Also, in generating first scan record 308, the data record protocol portion of the SDRP is applied to first x-ray scanning system 302 during the first scan. Specifically, the data record protocol portion is used to reconstruct a first 5-D voxelized representation of container 208 using first scan record 308. The first 5-D voxelized representation of container 208 includes a plurality of voxels.

In the first 5-D voxelized representation, the first three dimensions (X, Y, Z) are used to represent a spatial location of each voxel of the 5-D representation. Referring to XDI system 100 in FIG. 1, the primary x-ray beams 160 and low-angle scatter x-ray beams (not shown) are collimated by mechanical apertures in secondary collimator 120. Scatter is independently isolated from each object voxel representing container 208 and the contents therein. As used herein, the size of a typical voxel is approximately 1 cubic centimeter ($cm^3$) and is at least partially dictated by considerations of the time duration of the scan.

The fourth dimension represents a plurality of momentum transfer values (Q) defining a momentum transfer spectrum of container 208. The momentum transfer needed to alter the direction of flight of primary photons 160 on scattering, is determined by measuring the photon energy. XDI system 100 measures a diffraction profile from each object voxel. The momentum transfer is also related to lattice spacings of the object. The diffraction profiles from crystalline and non-crystalline material differ widely. The former yields diffraction peaks whose position on the momentum scale depends on lattice spacing. The latter provides broad peaks reflecting the statistical order present in liquid and amorphous substances. In the security application, approximately 20 features are extracted from XDI profiles for material characterization. These features include, but are not limited to, crystallinity, lattice spacings, orientation, scatter strength (density), fluidity, and mean atomic number.

The fifth dimension represents a plurality of angles of incidence ($\zeta$) of x-rays irradiating each voxel defined with respect to a system axis. In such angle-dependent XDI each voxel is struck by incoming radiation from several different directions. For amorphous materials and small-grain powders without a preferred orientation direction, the XDI profile is independent of irradiation direction. However, materials including an appreciable single-crystal component yield XDI profiles that depend on the irradiation direction, $\zeta$. Correlating the XDI profiles acquired at different values of $\zeta$ reveals the degree of anisotropy of the material under investigation.

In contrast to transmission x-ray techniques, which yield a signal dependent on 2 spatial dimensions, 5-D XDI delivers signals that, once reconstructed, have the capability to distinguish many more objects due to the higher dimensionality. As such, 5-D XDI is more sensitive to object properties and thus more suited than x-ray transmission to verifying whether an object under investigation is the authentic original, or whether it is an illegal copy or other such counterfeit.

To facilitate 5-D reconstruction of the first scan date, container handling system 300 uses the data record protocol portion of the SDRP implemented in first processing device 306. The data record protocol is applied to first x-ray scanning system 302 during the first scan. Specifically, the data record protocol is used to reconstruct the first five-dimensional (5-D) voxelized representation of container 208 using first scan record 308.

The data record protocol includes, but is not limited to, information such as, and without limitation, predefined parameters regarding voxel aggregation, data correction, and data reduction, i.e., feature extraction. As such, in the exemplary embodiment, container handling system 300, through the data record protocol implemented within first processing device 306 aggregates at least a portion of the plurality of voxels in the first 5-D voxelized representation of container 208. Also, container handling system 300, through the data record protocol, corrects at least a portion of data within at least one of first scan record 308 and second scan record 318. Further, container handling system 300, through the data record protocol, extracts at least a portion of data within at least one of first scan record 308 and second scan record 318. First scan record 308 includes the 5-D dependence of detector signals.

The data from the first scan are recorded, either as raw data or as data corrected for systematic errors, e.g., and without limitation, self-attenuation. The data can be rebinned into the aforementioned voxels if desired to reduce statistical photon noise. Also these voxels can be aggregated into groups of voxels to further reduce noise. Finally, to reduce the amount of data, features may be extracted from the first scan record 308. Regardless of the image reconstruction methods used and the methods of generating first scan record 308, a substantially similar SDRP will subsequently be used to generate second scan record 318.

Container 208 is moved 410 from first geographic location 304 to second geographic location 314. One example of moving container 208 includes shipping the container from any point on the globe to any other point on the globe through standard shipping and transport methods. Another, more limited example of handling container 208 is depositing container 208 in a storage facility for a temporary period of time at a first, i.e., depository point within the storage facility and withdrawing container 208 from the storage facility at a second, i.e., withdrawal point within the storage facility, where the depository points and the withdrawal points are located in separate sections of the storage facility.

A verification, i.e., second scan is performed 412 at second geographic location 314 using second x-ray scanning system 312. The second scan is performed in a manner substantially similar to the first scan. Specifically, container 208, whose contents are to be verified by comparison with first scan record 308 is placed, at a point-of-sale or the end-user, e.g., and without limitation, a hospital pharmacy, on conveyor belt 206 or support 116 of second x-ray scanning system 312 at the previously determined origin of coordinates using the same orientation with which container 208 was originally scanned. In case some displacement of the contents of the package has occurred in transit, it is possible with standard algorithms to perform rotational and/or translational adjustment of detector signals to give a best match with the signals acquired in the original scan. Alternatively, since the goods considered here have high street value, a form of packaging (e.g. foam cutout), which prevents relative movement of the package contents during travel can obviate the need for such displacement algorithms.

Second scan record 318 is generated 414 by second processing device 316 in a manner substantially similar as that for first scan record 308. Adhering to the pre-defined SDRP, the data are processed in exactly the same way for the second scan as for the first scan. This facilitates directly comparing first scan record 308 with second scan record 318. Also, the same data record protocol is used to reconstruct a second 5-D voxelized representation of container 208 using second scan record 318.

First scan record 308 and second scan record 318 are compared 416 to determine similarity, or lack thereof. To determine the similarity of the two data sets of first scan record 308 and second scan record 318, whether including raw data, corrected data, or extracted features, a binary classification scheme is used. The output of the binary classifier is simply yes/no dependent on whether or not second scan record 318 is deemed within noise limitations to be identical to first scan record 308. Any binary classifiers are used that enable operation of system 300 as described herein, including, without limitation, determining a normalized cross-correlation coefficient having a value of unity (1) if the five dimensional data sets of first scan record 308 and second scan record 318 are identical, decision trees, and Gaussian discriminate analysis (GDA).

Upon completion of comparing 416 first scan record 308 and second scan record 318, either second scan record 318 is determined 418 to be substantially indistinguishable from first scan record 310 or second scan record 318 is determined 420 to be substantially distinguishable from first scan record 308. As such, container handling system 300 facilitates determining if a package and its contents shipped from an origin, i.e., first geographic location 304 is the same package and contents arriving at second geographic location 314, or if somewhere in transit between locations 304 and 314, the package or its contents were intercepted and replaced with, for example, counterfeit articles.

FIG. 8 is an exemplary configuration 500 of a database 502 within a computing device 504, along with other related computing components, which may be used to perform a security inspection of container 208 (shown in FIGS. 3 and 4) with container handling system 300 (shown in FIG. 6) as described herein. Database 502 is coupled to several separate components within computing device 504, which perform specific tasks. In the exemplary embodiment, computing device 504 may be processing devices 306 and 316 (shown in FIG. 6), processing device 184 (shown in FIG. 1) for XDI-type systems, or, for CT-type imaging systems, any combination of control system 204, gantry controller 236, x-ray controller 238, conveyor controller 244, image reconstructor 242, and computer 246 (all shown in FIG. 4). Computing device 504 is configured to interface with a human system operator 505.

In the exemplary embodiment, database 502 includes first x-ray scanning system data 506 and second x-ray scanning system data 508. First x-ray scanning system data 506 includes information such as, without limitation, topology configuration information, x-ray power settings, and scatter detector information particular to first x-ray scanning system 302 (shown in FIG. 6). Second x-ray scanning system data 508 includes information such as topology configuration information, x-ray power settings, and scatter detector information particular to second x-ray scanning system 312 (shown in FIG. 6).

Computing device 504 includes database 502, as well as data storage devices 510. Computing device 504 also includes a SDRP component 512 for executing method step 402 (shown in FIG. 7), including receiving system data 506 and 508. Computing device 504 also includes an origin of coordinates component 514 for executing method step 404 (shown in FIG. 7). Computing device 504 further includes a first scan/first scan record component 516 for executing method steps 406 and 408 (both shown in FIG. 7). Computing device 504 also includes a container handling component 518 for executing method step 410 (shown in FIG. 7). Computing device 504 further includes second scan/second scan record component 520 for executing method steps 412 and 414 (both shown in FIG. 7). Computing device 504 also includes a first-to-second scan records comparison and determination component 522 for executing method steps 416, 418, and 420 (all shown in FIG. 7). A processing component 524 assists with execution of computer-executable instructions associated with container handling system 300 and method 400 as described herein.

The above described container handling systems facilitate cost-effective enhanced identification of counterfeit articles with a suitably high probability of detection ($P_D$) and low probability of false alarm, i.e., false positive ($P_{FA}$). Specifically, in contrast to many known x-ray scanning systems, the container handling systems as described herein facilitate distinguishing counterfeit products from authentic products with throughput that facilitates the pace of, e.g., cabin baggage screening (CBS) and hold baggage screening (HBS). More specifically, some of the container handling systems as described herein use multidimensional, i.e., four-dimensional (4-D) screening, i.e., three orthogonal spatial dimensions and an energy dimension using a computed tomography (CT) imaging system to screen the articles. Further, some of the container handling systems as described herein use multidimensional, i.e., five-dimensional (5-D) screening, i.e., three orthogonal spatial dimensions, a momentum dimension, and an angle of incidence dimension, using an x-ray diffraction imaging (XDI) system to screen the articles. A particular authentic package is scanned at it leaves, e.g., a production facility, in a pre-defined orientation and with a pre-defined scan and data record protocol (SDRP) using an XDI screener e.g., a CBS or a HBS, or a CT imaging system. A record is made of the multidimensional dependence of detector signals from this package. An arrangement is implemented to ensure that the same package is re-scanned at the point-of-sale or its receipt by the end user using the same orientation with which the package was originally scanned. The two sets of scanned multidimensional data are compared to authenticate the received package as the original package or not.

Exemplary embodiments of container handling systems are described above in detail. The methods and systems are not limited to the specific embodiments described herein, but rather, components of systems and/or steps of the methods may be utilized independently and separately from other components and/or steps described herein. For example, the methods may also be used in combination with other detection systems and methods, and are not limited to practice with only the detection systems and methods as described herein. Rather, the exemplary embodiment may be implemented and utilized in connection with many other x-ray-based security screening system applications.

Although specific features of various embodiments of the invention may be shown in some drawings and not in others, this is for convenience only. In accordance with the principles of the invention, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method of handling a container including at least one object therein, said method comprising:
    performing a first scan of the container comprising irradiating the container with polychromatic x-rays with a first x-ray scanning system at a first geographic location;
    generating, using at least one processing device, a first scan record;
    reconstructing a first multidimensional voxelized representation of the container using the first scan record, the first multidimensional voxelized representation including one of a four-dimensional (4-D) voxelized representation and a five-dimensional (5-D) voxelized representation;
    moving the container from the first geographic location to a second geographic location;
    performing a second scan of the container comprising irradiating the container with polychromatic x-rays with a second x-ray scanning system at the second geographic location;
    generating, using the at least one processing device, a second scan record;
    reconstructing a second multidimensional voxelized representation of the container using the second scan record, the second multidimensional voxelized representation including one of a 4-D voxelized representation and a 5-D voxelized representation;
    comparing the first scan record and the second scan record; and
    determining whether:
        the second scan record is substantially indistinguishable from the first scan record; or
        the second scan record is substantially distinguishable from the first scan record.

2. The method in accordance with claim 1 further comprising:
    implementing a scan record protocol; and
    applying the scan record protocol to the first x-ray scanning system during the first scan and applying the scan record protocol to the second x-ray scanning system during the second scan.

3. The method in accordance with claim 2, wherein the first x-ray scanning system and the second x-ray scanning system each include at least one x-ray tube and a conveyor belt, and wherein the scan record protocol includes predefined parameters for at least one of conveyor belt speed, conveyor belt speed distribution along a dimension substantially parallel to a direction of belt translation, an x-ray tube voltage, and an x-ray tube current.

4. The method in accordance with claim 3 further comprising establishing an origin of coordinates with respect to the conveyor belt for each of the first x-ray scanning system and the second x-ray scanning system.

5. The method in accordance with claim 2 further comprising:
    implementing a data record protocol; and
    applying the data record protocol to the first x-ray scanning system during the first scan and applying the data record protocol to the second x-ray scanning system during the second scan.

6. The method in accordance with claim 5, wherein the first multidimensional voxelized representation of the container and the second multidimensional voxelized representation of the container each includes a plurality of voxels.

7. The method in accordance with claim 6, wherein reconstructing the first multidimensional voxelized representation of the container using the first scan record and reconstructing the second multidimensional voxelized representation of the container using the second scan record comprises at least one of:
   aggregating at least a portion of the plurality of voxels in at least one of the first multidimensional voxelized representation of the container and the second multidimensional voxelized representation of the container;
   correcting at least a portion of data within at least one of the first scan record and the second scan record; and
   extracting at least a portion of data within at least one of the first scan record and the second scan record.

8. The method in accordance with Claim 1, wherein reconstructing the first and second multidimensional voxelized representation of the container includes reconstructing, using a computed tomography (CT) imaging system, a first three dimensions representing a spatial location of each voxel of the plurality of voxels, and a fourth dimension representing a plurality of energy values defining an energy spectrum of the polychromatic x-rays; and
   wherein reconstructing the first and second multidimensional voxelized representation of the container includes reconstructing, using an x-ray diffraction imaging (XDI) system, a first three dimensions representing a spatial location of each voxel of the plurality of voxels, a fourth dimension representing a plurality of momentum transfer values defining a momentum transfer spectrum of the container, and a fifth dimension representing a plurality of angles of incidence of x-rays irradiating each voxel of the plurality of voxels defined with respect to a system axis.

9. The method in accordance with claim 7, wherein the data record protocol includes predefined parameters for voxel aggregation, data correction, and data extraction.

10. The method in accordance with claim 1, wherein determining the second scan record is substantially indistinguishable from the first scan record comprises determining the container and the at least one object therein received at the second geographic location are substantially identical to the container and the at least one object therein shipped from the first geographic location.

11. The method in accordance with claim 1, wherein determining the second scan record is substantially distinguishable from the first scan record comprises determining the container and the at least one object therein received at the second geographic location are not the container and the at least one object therein shipped from the first geographic location.

12. A container handling system comprising:
   at least one processing device;
   a first x-ray scanning system at a first geographic location coupled to said at least one processing device, said first x-ray scanning system configured to perform a first x-ray scan of a container, said at least one processing device configured to generate a first scan record of the container;
   a second x-ray scanning system at a second geographic location coupled to said at least one processing device, said second x-ray scanning system configured to perform a second x-ray scan of the container; and
   a communication channel between the first x-ray scanning system and the second x-ray scanning system, and
   said at least one processing device further configured to:
      reconstruct a first multidimensional voxelized representation of the container using the first scan record, the first multidimensional voxelized representation including one of a four-dimensional (4-D) voxelized representation and a five-dimensional (5-D) voxelized representation;
      generate a second scan record of the container;
      reconstruct a second multidimensional voxelized representation of the container using the second scan record, the second multidimensional voxelized representation including one of a 4-D voxelized representation and a 5-D voxelized representation;
      compare the first scan record and the second scan record; and
      determine whether:
         the container scanned at the second geographic location is substantially indistinguishable from the container scanned at the first geographic location; or
         the container scanned at the second geographic location is distinguishable from the container scanned at the first geographic location.

13. The container handling system in accordance with claim 12, said at least one processing device further configured to:
   implement a scan record protocol; and
   apply the scan record protocol to said first x-ray scanning system during the first scan and apply the scan record protocol to said second x-ray scanning system during the second scan.

14. The container handling system in accordance with claim 13, wherein said first x-ray scanning system and said second x-ray scanning system each include at least one x-ray tube and a conveyor belt, and wherein the scan record protocol includes predefined parameters for at least one of a speed of said conveyor belt, a speed distribution along a dimension substantially parallel to a direction of translation of said conveyor belt, a voltage of said x-ray tube, and a current of said x-ray tube.

15. The container handling system in accordance with claim 14 further comprising an established origin of coordinates with respect to said conveyor belt for each of said first x-ray scanning system and said second x-ray scanning system.

16. The container handling system in accordance with claim 13, said at least one processing device further configured to:
   implement a data record protocol; and
   apply the data record protocol to said first x-ray scanning system during the first scan and apply the data record protocol to said second x-ray scanning system during the second scan;
   wherein the first multidimensional voxelized representation of the container and the second multidimensional voxelized representation of the container each includes a plurality of voxels.

17. The container handling system in accordance with claim 16, said at least one processing device further configured to:
   aggregate at least a portion of the plurality of voxels in at least one of the first multidimensional voxelized representation of the container and the second multidimensional voxelized representation of the container;

correct at least a portion of data within at least one of the first scan record and the second scan record; and extract at least a portion of data within at least one of the first scan record and the second scan record, wherein the data record protocol includes predefined parameters for voxel aggregation, data correction, and data extraction.

18. The container handling system in accordance with claim 17, said at least one processing device further configured to reconstruct the first multidimensional voxelized representation of the container and reconstruct the second multidimensional voxelized representation of the container through one of:

reconstructing the first and second multidimensional voxelized representation of the container using a computed tomography (CT) imaging system, wherein a first three dimensions represent a spatial location of each voxel of the plurality of voxels, and a fourth dimension represents a plurality of energy values defining an energy spectrum of the polychromatic x-rays; and reconstructing the first and second multidimensional voxelized representation of the container using an x-ray diffraction imaging (XDI) system, wherein a first three dimensions represent a spatial location of each voxel of the plurality of voxels, a fourth dimension represents a plurality of momentum transfer values defining a momentum transfer spectrum of the container, and a fifth dimension represents a plurality of angles of incidence of x-rays irradiating each voxel of the plurality of voxels defined with respect to a system axis.

19. The container handling system in accordance with claim 12, wherein determining the second scan record is substantially indistinguishable from the first scan record comprises determining the container and the at least one object therein received at the second geographic location are substantially identical to the container and the at least one object therein shipped from the first geographic location.

20. The container handling system in accordance with claim 12, wherein determining the second scan record is substantially distinguishable from the first scan record comprises determining the container and the at least one object therein received at the second geographic location are not the container and the at least one object therein shipped from the first geographic location.

21. The container handling system in accordance with claim 12, wherein said first x-ray scanning system is one of an x-ray diffraction imaging (XDI) system or a computed tomography (CT) imaging system.

22. The container handling system in accordance with claim 12, wherein said first x-ray scanning system is a multiple inverse fan beam (MIFB) x-ray diffraction imaging (XDI) system.

* * * * *